United States Patent
Kato et al.

(10) Patent No.: US 10,607,720 B2
(45) Date of Patent: Mar. 31, 2020

(54) ASSOCIATING GENE EXPRESSION DATA WITH A DISEASE NAME

(71) Applicant: INTERNATIONAL BUSINESS MACHINES CORPORATION, Armonk, NY (US)

(72) Inventors: Linda H. Kato, San Jose, CA (US); Jeffrey T. Kreulen, San Jose, CA (US); Jacques Labrie, Sunnyvale, CA (US); William S. Spangler, San Martin, CA (US); Ignacio G. Terrizzano, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 652 days.

(21) Appl. No.: 15/151,595

(22) Filed: May 11, 2016

(65) Prior Publication Data

US 2017/0329900 A1  Nov. 16, 2017

(51) Int. Cl.
  *G16B 40/00* (2019.01)
  *G16B 35/00* (2019.01)
  *G16C 20/60* (2019.01)
  *G16B 25/10* (2019.01)

(52) U.S. Cl.
  CPC ............ *G16B 40/00* (2019.02); *G16B 25/10* (2019.02); *G16B 35/00* (2019.02); *G16C 20/60* (2019.02)

(58) Field of Classification Search
  CPC ........................................................ G06F 19/24
  See application file for complete search history.

(56) References Cited

U.S. PATENT DOCUMENTS

| | | |
|---|---|---|
| 2003/0009296 A1 | 1/2003 | Sabatini et al. |
| 2003/0054394 A1 | 3/2003 | Chin et al. |
| 2003/0219771 A1 | 11/2003 | Bevilacqua et al. |

(Continued)

FOREIGN PATENT DOCUMENTS

| | | |
|---|---|---|
| WO | 02090589 A1 | 11/2002 |

OTHER PUBLICATIONS

Nitsch et al., PINTA: a web server for network-based gene prioritization from expression data, Nucleic Acids Res. Jul. 2011;39(Web Server issue):W334-8. doi: 10.1093/nar/gkr289. Epub May 20, 2011.*

(Continued)

*Primary Examiner* — Aaron A Priest
(74) *Attorney, Agent, or Firm* — Reza Sarbakhsh

(57) ABSTRACT

The present invention relates to a method and system for associating gene expression data with a disease name. A first data set associated with a plurality of genetic probes for a plurality of biological samples may be received. The first data set may be sorted based on a normalized gene expression values for the plurality of genetic probes. A largest value gap of the normalized gene expression values may be identified. A set of expressed genes within the first data set may be identified. An indexable document may be generated for a biological sample of the plurality of biological samples comprising data associated with the set of expressed genes. A second data set associated with an expressed gene of the set of expressed genes may be searched. A disease name may be associated with an expressed gene based on a threshold correlation between the disease name and the expressed gene.

20 Claims, 11 Drawing Sheets

| Sample | Value |
|---|---|
| GSM550796 | 1364.64 |
| GSM550839 | 1429.90 |
| GSM550835 | 1435.95 |
| GSM550789 | 1463.26 |
| GSM550916 | 1491.08 |
| GSM550796 | 1651.95 |
| GSM550839 | 1653.59 |
| GSM550835 | 1655.46 |
| GSM550789 | 1670.74 |
| GSM550916 | 1683.57 |

(56) References Cited

U.S. PATENT DOCUMENTS

| | | |
|---|---|---|
| 2004/0024543 A1 | 2/2004 | Zhang et al. |
| 2005/0233310 A1 | 10/2005 | Hampson et al. |
| 2007/0027630 A1 | 2/2007 | Sanchez |
| 2008/0318218 A1 | 12/2008 | Frudakis |
| 2011/0003294 A1 | 1/2011 | Liew |
| 2011/0171650 A1 | 7/2011 | Conrad et al. |

OTHER PUBLICATIONS

Zhang, A comprehensive evaluation of SAM, the SAM R-package and a simple modification to improve its performance, BMC Bioinformatics. 2007; 8: 230. Published online Jun. 29, 2007.*

Sirota et al., "Discovery and preclinical validation of drug indications using compendia of public gene expression data," NIH Public Access, Author Manuscript, Published in final edited form as: Sci Transl Med., Aug. 17, 2011, 3(96): 96ra77. doi:10.1126/scitranslmed.3001318, pp. 1-22.

Subramanian et al., "Gene set enrichment analysis: A knowledge-based approach for interpreting genome-wide expression profiles," PNAS, Oct. 25, 2005, vol. 102, No. 43, pp. 15545-15550.

Jenssen et al., "A literature network of human genes for high-throughput analysis of gene expression," Nature Genetics, vol. 28, May 2001, Copyright 2001 Nature Publishing Group, pp. 21-28.

Pan et al., "Pathway Analysis for Drug Repositioning Based on Public Database Mining," Journal of Chemical Information and Modeling, 2014, vol. 54, ACS Publications, Copyright 2014 American Chemical Society, pp. 407-418.

Spangler, "Accelerating Discovery: Mining Unstructured Information for Hypothesis Generation," Series: Chapman & Hall/CRC Data Mining and Knowledge Discovery Series, Published Oct. 9, 2015, Abstract Summary, Printed on Feb. 29, 2016, pp. 1-2.

Mell et al., "The NIST Definition of Cloud Computing," National Institute of Standards and Technology, U.S. Department of Commerce, Special Publication 800-145, Sep. 2011, pp. 1-7.

Croset, "Drug repositioning and indication discovery using description logics," University of Cambridge, A thesis submitted on Mar. 2014, for the Degree of Doctor of Philosophy, Samuel Claude Jean Croset, Darwin College, pp. 1-228.

Iorio et al., "Transcriptional data: a new gateway to drug repositioning?" Drug Discovery Today, vol. 18, Nos. 7/8, Apr. 2013, Elsevier Ltd., pp. 350-357.

Qabaja et al., "Prediction of novel drug indications using network driven biological data prioritization and integration," Journal of Chem Informatics 20146:1, Published Jan. 7, 2014, Printed on May 3, 2016, pp. 1-13.

Jegga et al., "Orphan Diseases, Bioinformatics and Drug Discovery", Chapter 16: Pediatric Biomedical Informatics: Computer Applications in Pediatric Research, Series Note: Translational Bioinformatics, 2213-2775, vol. 2, Imprint: Dordrecht; New York; Springer 2012, pp. 287-307.

* cited by examiner

| Sample | Value |
|---|---|
| GSM550796 | 1364.64 |
| GSM550839 | 1429.90 |
| GSM550835 | 1435.95 |
| GSM550789 | 1463.26 |
| GSM550916 | 1491.08 |

202

| | |
|---|---|
| GSM550796 | 1651.95 |
| GSM550839 | 1653.59 |
| GSM550835 | 1655.46 |
| GSM550789 | 1670.74 |
| GSM550916 | 1683.57 |

FIG. 2B

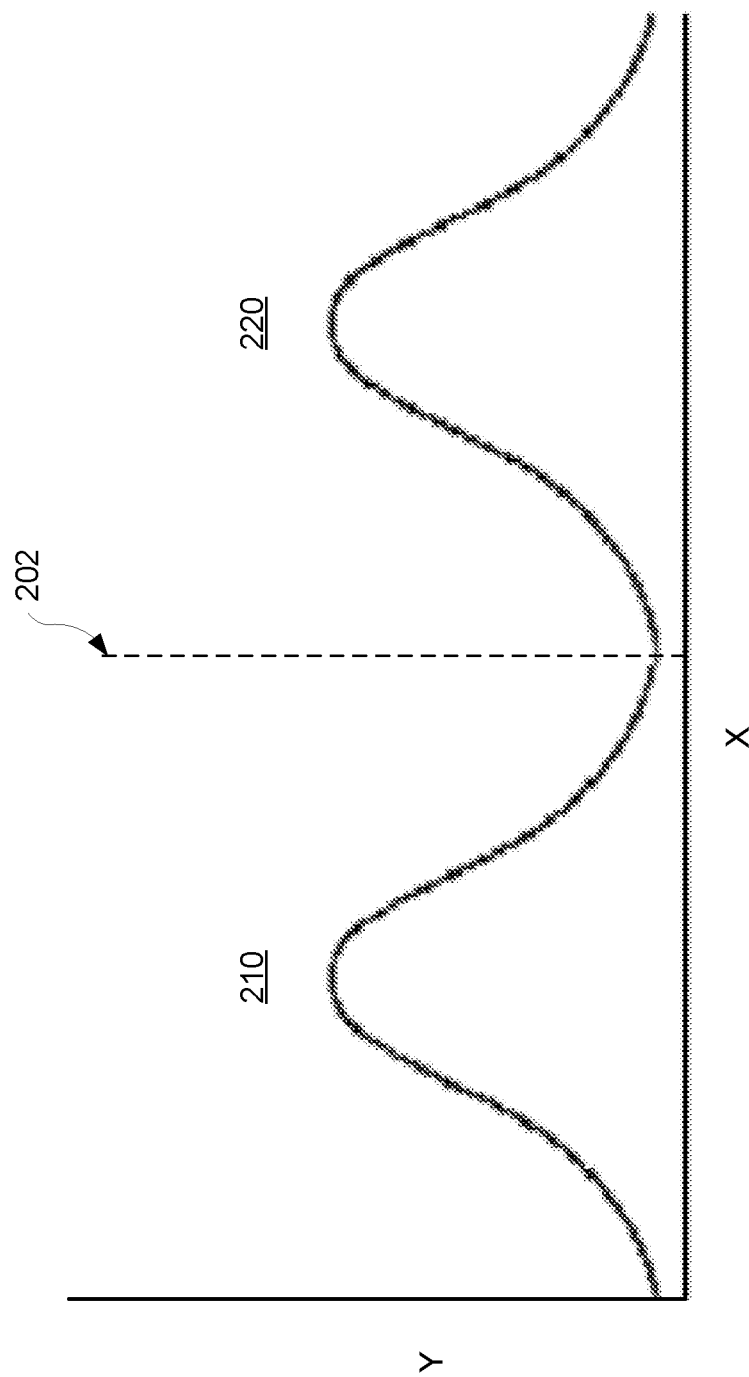

| Expressed Genes | Gene Expression Value |
|---|---|
| IGF2 | 1364.64 |
| H3F3AP4 | 2146.98 |
| CD44 | 794.21 |
| GAPDH | 1195.03 |
| ACTB | 1954.97 |

Indexable document for GSM550796

FIG. 2D

| Disease | Number of Samples with Disease | Number of Samples with Gene and Disease | Percent of Samples with Disease having Gene | Expected Number of Samples with Gene and Disease |
|---|---|---|---|---|
| Carcinoma | 31,663 | 3,991 | 12.6 | 2,376.57 |
| Breast Neoplasms | 41,214 | 3,842 | 9.32 | 3,093.45 |
| Colorectal Neoplasms | 7,940 | 1,805 | 22.73 | 595.96 |
| Inflammation | 30,592 | 1,793 | 5.86 | 2,296.18 |
| Leukemia | 25,780 | 927 | 3.6 | 1,935 |

FIG. 3A

| Gene | Number of Samples with Gene | Number of Samples with Gene and Disease | Percent of Samples with Gene Having Disease | Expected Number of Samples with Gene and Disease |
|---|---|---|---|---|
| IGFBP5 | 51,177 | 879 | 1.72% | 519.01 |
| H3F3AP4 | 52,569 | 888 | 1.69% | 533.13 |
| CD44 | 69,193 | 962 | 1.39% | 701.72 |
| GAPDH | 117,220 | 1055 | 0.9 | 1,188.79 |
| ACTB | 113,375 | 859 | 0.76% | 1,149.8 |

FIG. 3B 100,607,720 B2

ASSOCIATING GENE EXPRESSION DATA WITH A DISEASE NAME

BACKGROUND

The present invention relates generally to the field of computing, and more particularly to a method and system for associating gene expression data with a disease name.

Treatments for some diseases may operate by targeting a particular protein. For example, an antibody may target a particular protein generated by a cancer. HER-2 is a gene expressed in many breast cancers, and the monoclonal antibody trastuzumab may be effective against certain types of breast cancer cells that express HER-2. Current approaches to discover treatments may involve studying protein and tumor properties.

SUMMARY

Embodiments of the present invention disclose a method for associating gene expression information with a disease name. The method may include receiving a first data set associated with a plurality of genetic probes for a plurality of biological samples. The method may include sorting the first data set based on a normalized gene expression values for the plurality of genetic probes. The method may include identifying a largest value gap of the normalized gene expression values; identifying a set of expressed genes within the first data set. Identifying the set of expressed genes may include converting the normalized gene expression values to binary expressions. The method may include generating an indexable document for a biological sample of the plurality of biological samples including data associated with the set of expressed genes. The method may include searching a second data set associated with an expressed gene of the set of expressed genes. Searching the second data set may include identifying a set of disease names associated with the expressed gene. The method may include associating at least one disease name of the set of disease names with at least one expressed gene of the set of expressed genes based on a threshold correlation between the at least one disease name and the at least one expressed gene.

Embodiments of the present invention disclose a computer program product for associating gene expression information with a disease name. The computer program product may include a computer readable storage medium having program instructions embodied therewith. The computer readable storage medium is not a transitory signal per se. The program instructions may be executable by a computer to cause the computer to perform a method. The method may include receiving a first data set associated with a plurality of genetic probes for a plurality of biological samples. The method may include sorting the first data set based on a normalized gene expression values for the plurality of genetic probes. The method may include identifying a largest value gap of the normalized gene expression values; identifying a set of expressed genes within the first data set. Identifying the set of expressed genes may include converting the normalized gene expression values to binary expressions. The method may include generating an indexable document for a biological sample of the plurality of biological samples including data associated with the set of expressed genes. The method may include searching a second data set associated with an expressed gene of the set of expressed genes. Searching the second data set may include identifying a set of disease names associated with the expressed gene. The method may include associating at least one disease name of the set of disease names with at least one expressed gene of the set of expressed genes based on a threshold correlation between the at least one disease name and the at least one expressed gene.

Embodiments of the present invention disclose a computer system for associating gene expression information with a disease name. The computer system may include one or more computer processors, one or more computer-readable storage media, and program instructions stored on the computer-readable storage media for execution by at least one of the one or more processors. The program instructions may include instructions to receive a first data set associated with a plurality of genetic probes for a plurality of biological samples. The program instructions may include instructions to sort the first data set based on a normalized gene expression values for the plurality of genetic probes. The program instructions may include instructions to identify a largest value gap of the normalized gene expression values. The program instructions may include instructions to identify a set of expressed genes within the first data set. The instructions to identify the set of expressed genes may include instructions to convert the normalized gene expression values to binary expressions. The program instructions may include instructions to generate an indexable document for a biological sample of the plurality of biological samples comprising data associated with the set of expressed genes. The program instructions may include instructions to search a second data set associated with an expressed gene of the set of expressed genes. The instructions to search the second data set may include identifying a set of disease names associated with the expressed gene. The program instructions may include instructions to associate at least one disease name of the set of disease names with at least one expressed gene of the set of expressed genes based on a threshold correlation between the at least one disease name and the at least one expressed gene.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings.

FIGS. 2A-2F are illustrations of a document build process, in accordance with an embodiment of the present invention.

FIGS. 3A-3B are illustrations of generated associations between an expressed gene and a disease, in accordance with an embodiment of the present invention.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
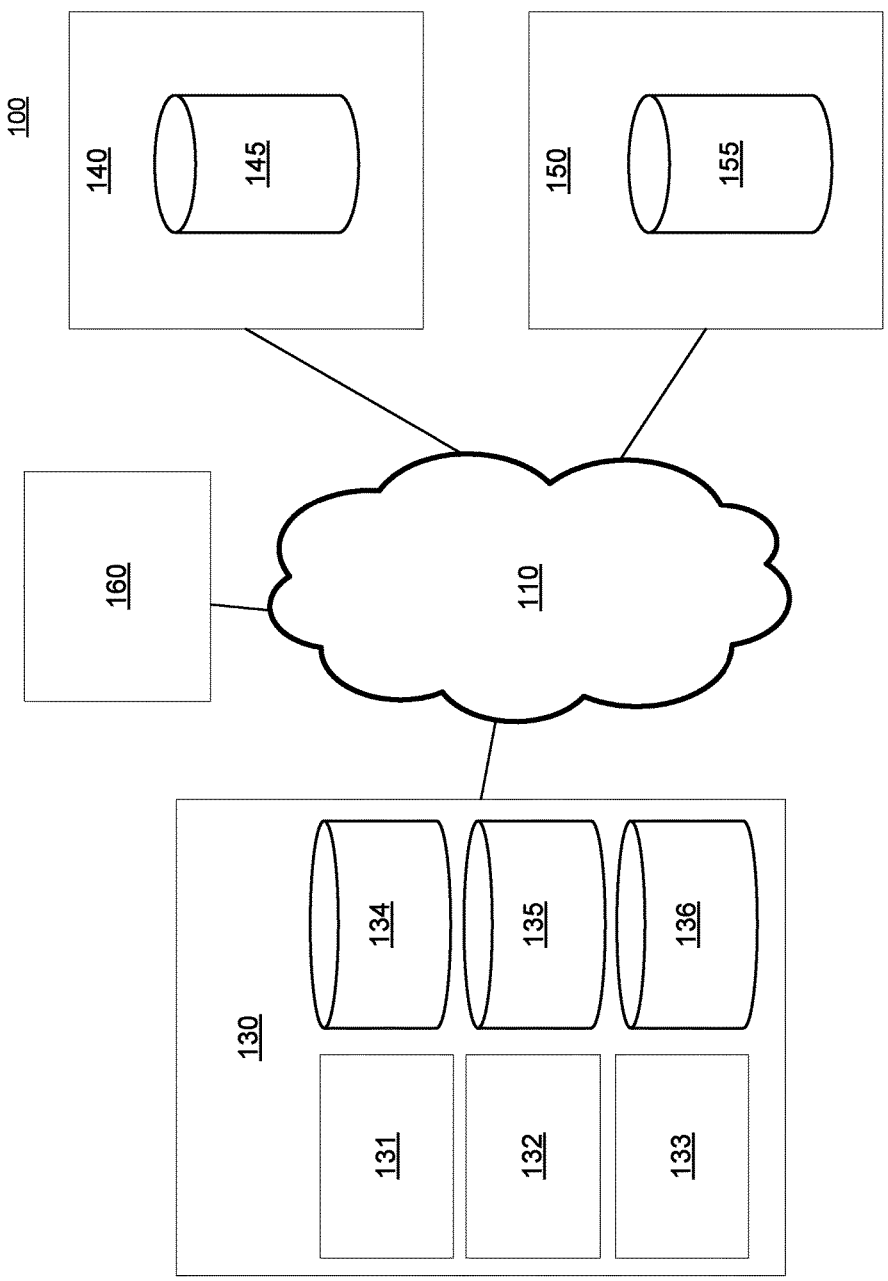
FIG. 1 is a functional block diagram illustrating an alternative indication identification system, in accordance with an embodiment of the present invention.

Embodiments of the present invention may provide a system and method for identifying alternative indications for pharmaceuticals. Alternative indications may be used if an antibody is known to be effective against a certain disease may also be effective for other types of diseases. If an antibody that may be effective against a particular protein for one type of cancer is known, additional cancers that antibody may be effective in treating may be identified. Embodiments of this invention include a discovery system and method for utilizing gene expression data and indexed medical articles to accelerate identifying alternative indications of drugs.

Determining whether an antibody is effective against a particular protein from a first type of cancer may be effective against a protein from another cancer may increase treatment options. For example, HER-2 is a gene expressed in many breast cancers, and monoclonal antibody trastuzumab may be effective in treating certain types of breast cancer cells that express HER-2. Thus, treating other cancers with trastuzumab may be an alternative indication for trastuzumab. An alternative indication for a pharmaceutical may include an unconventional treatment for a disease using the pharmaceutical. Current approaches to discovering alternative indications may involve studying protein and tumor properties, while excluding (or generalizing) gene expression data obtained from studies. The data obtained from studies may be publically available, but the data may be contained in a siloed environment(s), where cross-study and cross-source references are not included, possibly due to the challenge of cross-referencing an enormous amount of data. For example, gene expression data available from the National Center of Biotechnology Information's (NCBI) Gene Expression Omnibus (GEO) may not be cross-referenced with any published medical text data (e.g., Medline® abstracts and/or articles). Thus, a system and method for cross-referencing gene expression data with published medical text data is needed.

Embodiments of the present invention may identify alternative indication(s) for a pharmaceutical by defining a gene selection mechanism and cross referencing it with medical literature. Embodiments of the present invention may accelerate discovery of alternative indications and/or discover alternative indications that may not have otherwise been discovered. A genetic profile of one or more patients may be included in the analysis, thus rendering more accurate alternative indication predictors. Embodiments of the present invention may include a method of cross-referencing microarray, sequencing, and other genomic data (consisting of thousands of gene expression data sets for numerous of tumors and other diseases) with text data from other sources (e.g. Medline® publications), so that the context of a biological sample being studied can be obtained by leveraging analytical tools over a wide array of data. Embodiments of the invention may operate by using gene expression information in conjunction with text information about the indication (i.e. disease or tumor). Embodiments of the present invention may use source information to create indexable document(s) for a biological sample (or plurality of biological samples), the documents containing information about the biological sample (e.g., age of patient, gender of patient, symptoms of patient, location of sample extraction, etc.) as well as the genes that the biological sample expressed. In an embodiment, the indexable document(s) may be derived from analyzing data from numerous disease studies conducted on a varying number of patients ranging from approximately one to approximately thousands, and ranges therebetween. Biological sample data may be obtained from one or more disease studies. Biological sample data, may include, for example, data associated with a patient's characteristics along with corresponding readings from several thousand probes which are used to map to expressed genes. A selection algorithm may be applied to the probe data to comparatively (between patients with the same disease) determine genes that are 'expressed'. Expressed genes may be mapped to one or more corresponding genes based on the appropriate sequencing platform. Using the mapped genes, indexable documents may be created to establish relationships between diseases and genes, which can be cross-referenced with external data (e.g., Medline® publications). Embodiments of the present invention will now be described in detail with reference to FIGS. 1-7.

FIG. 1 is an alternative indication identification system 100, according to an aspect of the invention. In an exemplary embodiment, the alternative indication identification system 100 may include a network 110, computing device 130, one or more servers (e.g., server 140 and server 150), and a deoxyribonucleic acid (DNA) sequencer 160. The alternative indication identification system 100 may include an alternative indication identification application. The alternative indication identification application may be a program, function, or module of a computer program (not shown) executable by a processor of the alternative indication identification application system 100. The alternative indication identification system 100 may be implemented using a computing node such as the computing node of FIG. 5.

Computing device 130 may be a laptop computer, tablet computer, netbook computer, personal computer (PC), desktop computer, smart phone, or any programmable electronic device. Computing device 130 may include internal and external hardware components, as depicted and described in further detail with respect to FIG. 5. Computing device 130 may include the alternative indication identification application. Computing device 130 may include one or more databases (e.g., a first database 134 and a second database 135). Computing device 130 may include one or more electronic documents (e.g., document 131, document 132, and document 133) stored in one or more databases. Computing device 130 may include one or more communication devices may include any communication device known in the art, such as, for example, a Bluetooth device, WiFi device, near-field communication (NFC) device, radio frequency device, or any combination thereof. The one or more communication devices may be used to transmit and/or receive data from the server 140 and/or the server 150 via the network 110.

Network 110 may be any combination of connections and protocols that will support communications between computing device 130 and one or more servers (e.g., server 140 and server 150). In an embodiment, network 110 may be the Internet, representing a worldwide collection of networks and gateways to support communications between devices connected to the Internet. Network 110 may include, for example, wired, wireless or fiber optic connections. In other embodiments, network 110 may be implemented as an intranet, a local area network (LAN), a wide area network (WAN), or a combination thereof. Network 110 may include wired connections, wireless connections, fiber optic connections, or a combination thereof.

The server 140 may include one or more databases (e.g., a database 145). Database 145 may include structured and/or unstructured data associated with, for example, biomedical and genomic information. Unstructured data may include text documents in any format known in the art, such as, for example, spreadsheet (e.g., .xls), Portable Document Format (PDF), word processing document (e.g., .doc), HyperText Markup Language (HTML), etc. In an embodiment, the server 140 may be operated and/or managed by the National Center for Biotechnology Information (NCBI). For example, the database 145 may be the Gene Expression Omnibus (GEO). GEO is a public functional genomics data repository including array-based and sequence-based data. GEO data may include tables containing floating point gene-expression values for every gene for every patient in a study. The number of rows in the table may represent the number of probes that are measured by a genetic sequencing apparatus. The number of columns may be the number of tumor samples that are sequenced in a study. A probe may correspond to one or more genes, and sometimes more than one probe may point to a same gene.

The server 150 may include one or more databases (e.g., a database 155). Database 155 may include unstructured data associated with, for example, medical literature. The unstructured data may include text documents in any format known in the art, such as, for example, spreadsheet (e.g., .xls), Portable Document Format (PDF), word processing document (e.g., .doc), HyperText Markup Language, etc. In an embodiment, the server 150 may be operated and/or managed by Medline® Industries, Inc.

The DNA sequencer 160 may include an automated electrophoresis system to detect migration of labelled DNA fragments. The DNA fragments may be labelled by a hybridization probe including a fragment of DNA or RNA of variable length (e.g., 100-1000 bases long) and a molecular marker. The molecular marker may be, for example, a radioactive marker, fluorescent marker, or a combination thereof. The DNA sequencer 160 may utilize autoradiography or other imaging techniques. The DNA sequencer 160 may include a database to store information associated with identified genes, such as, for example, nucleotide sequence and location.

FIGS. 2A-2F are illustrations of a document build process, according to an embodiment of the present invention. In an embodiment, NCBI GEO data may be converted into a format that may be represented by a document by implementing a document build process. The document build process may include (1) receiving gene expression data (e.g., from NCBI studies) having data associated with a plurality of biological samples (e.g., from a plurality of patients) and a plurality of probes, (2) sorting gene expression data based on a normalized expression intensity for a plurality of probes, (3) omitting outlier values from the gene expression data, (4) identifying expressed genes (e.g., by identifying a gap in gene intensity values and converting numerical values to binary "expressed" or "unexpressed" values), (5) selecting names of expressed genes (e.g., based on gene ontology), and building an expression profile for a patient of the plurality of patients. Embodiments may include building predictive models based on patient characteristics identified in the expression profile for a patent.

Figure 2A:
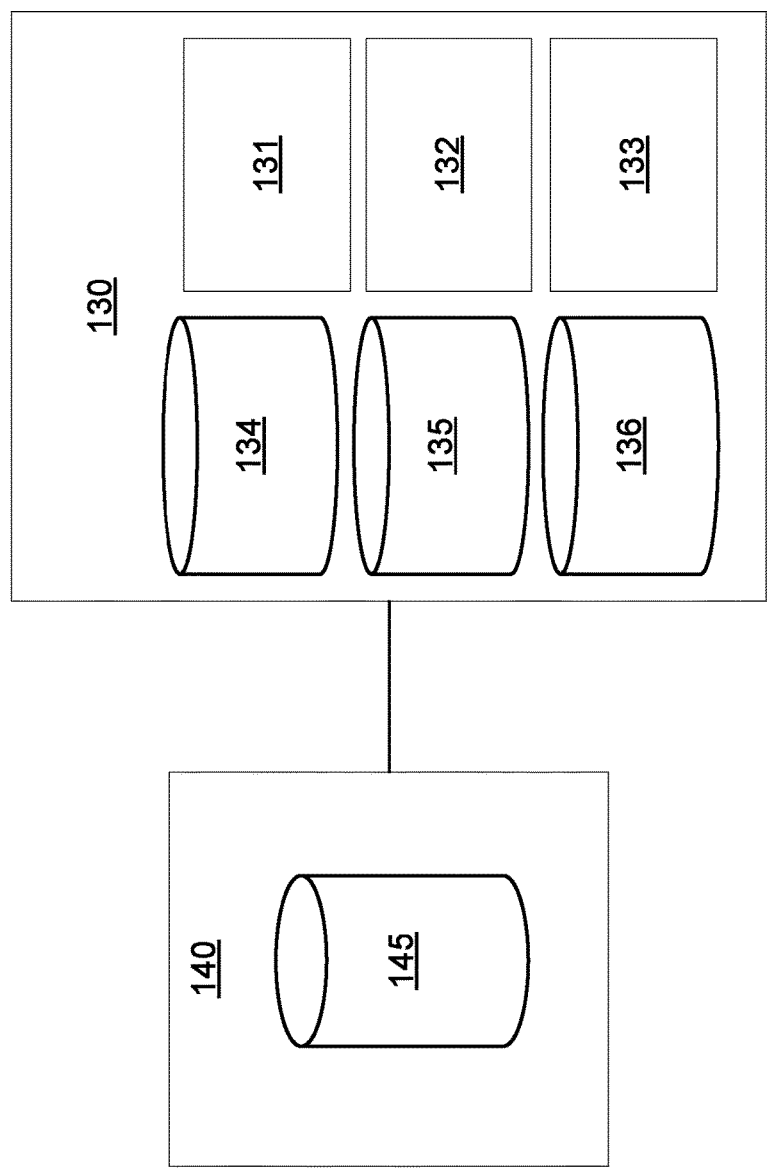

FIG. 2A illustrates receiving, by the computing device 130, probe expression data from the server 140, according to an embodiment of the present invention. The received gene expression data may be stored in the first database 134. The data may include tables containing floating point gene-expression values for a plurality of genes for plurality of patients in a study. The number of rows in the table may represent a number of probes that may be measured by a genetic sequencing apparatus. The number of columns may be the number of tumor samples that may be sequenced in a study. A probe may correspond to one or more genes, and sometimes more than one probe may point to a same gene. In an embodiment, probe expression data across patients (samples) in a study may be received from a server (e.g., the server 140). The probe expression data may be stored in the first database 134.

FIG. 2B illustrates gene expression data associated with a plurality of samples in a database. In an embodiment, gene expression data in the first database 134 may be sorted. A processor of the computing device 130 may sort the probe expression data from highest to lowest for the plurality of patients. The sorted probe expression data may be stored in the first database 134 and/or another database. In an embodiment, a processor of the computing device 130 may omit high and low value outliers from the sorted probe expression data. For example, approximately three high outliers and approximately three low outliers may be omitted.

In an embodiment, a processor of the computing device 130 may assign a score for a set of the probe expression data 130 by subtracting a lowest non-outlier value from a highest non-outlier value. The score may indicate which genes of the set of probe expression data are most differentially expressed. The top scoring (i.e. the most differentially expressed) set of probe expression data may be used to define a feature space. The feature space may include scored sets of probe expression data in increasing order. The feature space may be stored in the first database 134 and/or another database. By identifying which genes may be most differentially expressed, genes having only small differences across patient populations may be ignored. Genes with only small differences across patient populations may be attributable to noise variables. Thus, by identifying genes that are most differentially expressed, much of the noise may be eliminated and false correlations may be reduced. A gap 202 may be a largest difference between consecutive scores.

FIG. 2C is an illustration of a bimodal distribution of gene expression values, according to an embodiment of the present invention. In an embodiment, expressed genes may be identified by examining a bimodal distribution of gene expression values. In an embodiment, a bimodal distribution of gene expression values may be assumed. The bimodal distribution of gene expression data is illustrated in FIG. 2C with a first bump (i.e. a first series of consecutive gene expression values) and a second bump (i.e. a second series of consecutive gene expression values) separated by gap 202 (i.e. a largest difference in consecutive scores). The first bump may lie within region 210 and the second bump may lie within region 220. Region 210 and region 220 may be separated by a vertical dashed line. A y-axis of the graph may represent differential expression scores and the x-axis may represent gene expression values.

Scored sets of probe expression data may be analyzed to determine which genes are expressed and which genes are not expressed. Scored sets of probe expression data may be analyzed by identifying a largest gap in consecutive scores. In cases where probe expression data is highly associated with a disease, the probe expression data may include one phenotype represented by one of these bumps (i.e. a first series of high gene expression values), and a second phenotype represented by another bump (i.e. a second series of high gene expression values). Note that it is most typical for genes to have exactly two phenotypes. In cases where more than two phenotypes exist, more bumps may exist. In cases with multiple bumps, a deepest valley between bumps may be used to identify which genes are expressed.

A largest gap between gene expression data which may not be expressed and gene expression data which may be expressed is represented by a dashed line in the valley (i.e. gap 202) between the first and second bump. Some genes may have a robust bimodal expression pattern. For example, some genes associated with certain cancers may behave as molecular switches, with on and off expression states. Probes having scores above the gap (i.e. within region 220) may be identified as expressed. In an area between the bumps, expression values may tend to be thinly populated (i.e. more sparse than adjacent regions) along the x axis (which is the gene expression value). Therefore, the data may be divided into "expressed" and "unexpressed" at the gap 202. This may be where phenotypes may be distinguished based on gene expression values. Higher than the gap 202 (i.e. region 220) may be one phenotype and lower than the gap 202 (i.e. region 210) may be another phenotype.

A name associated with a gene probe (e.g., GSM550796) may be converted into a name associated with a gene (e.g., IGF2). A corresponding sequencing platform may be used to identify a name associated with a gene that corresponds to a gene probe. A name of a gene may be identified by extracting data associated with GO Ontology descriptions.

Identifying bimodal expression patterns in genes may aid in the search for clinically important therapeutic targets for various diseases (e.g., cancer). Typically, determining a factor that can characterize samples that belong to each of two distributions may be difficult. However, utilizing the method described above may facilitate identifying "expressed" and "unexpressed" genes based on gene expression data with greater speed and accuracy than prior methods.

FIG. 2D illustrates an indexable document generated for a sample, according to an embodiment of the present invention. An indexable document may be generated for a biological sample (e.g., a sample from a patient) of the plurality of biological samples associated with gene expression data. The indexable document may include, for example, text from one or more studies, data associated with a set of expressed genes, and canonical disease names. For example, the indexable document may be generated for sample GSM550796 and incorporate all or a set of the genes identified in the sample. Sample GSM550796 may have a gene expression value for IGF2 of 1364.64, a gene expression value for H3F3AP4 of 2146.98, a gene expression value for CD44 of 794.21, a gene expression value for GAPDH of 1195.03, and a gene expression value for ACTB of 1954.97. The indexable document may be indexed by a search server, such as, for example, SOLR or elasticsearch. In an embodiment, the indexable document may include reference data associated with the feature space. The reference data may be used to identify relationships and/or patterns in the gene expression data. In an embodiment, medical literature (e.g., Medline® text information) may be indexed to enable cross referencing between gene expression data and medical literature. In an embodiment, the indexable document may be combined with indexed medical literature (e.g., Medline® text information). The external medical literature may be unstructured data (e.g., plain language text). The unstructured data may be structured using natural language processing to make the data accessible to a computing device (e.g., the computing device 130).

The indexable document may be used in one or more implementations, such as, for example, identifying associations between an expressed gene of a biological sample and a disease name. Embodiments of various implementations for the indexable document are described below with reference to FIGS. 3A-3B.

Figure 2E:
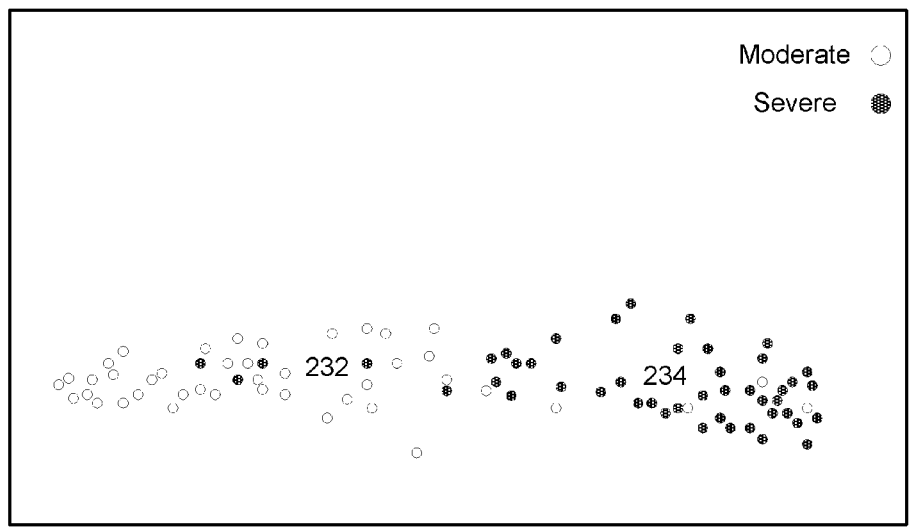
Figure 2F:
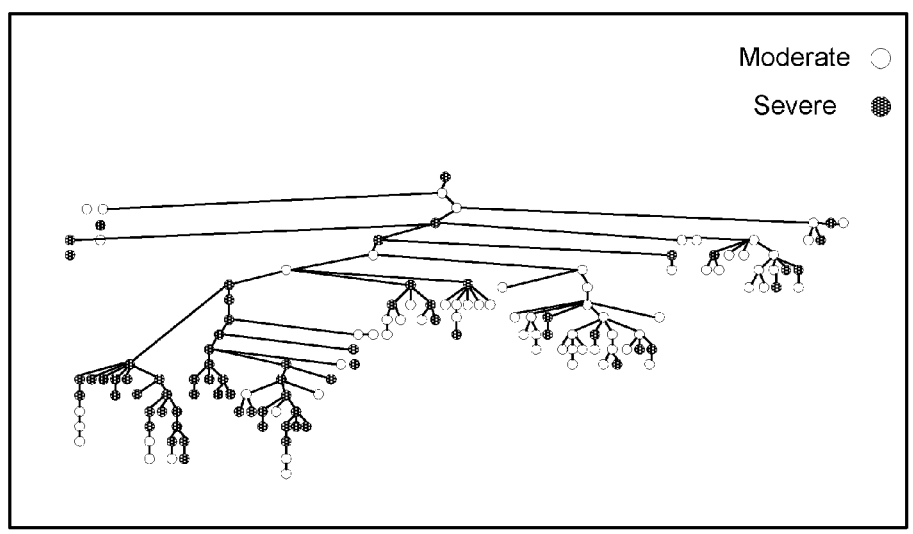

FIGS. 2E-2F are illustrations of a feature space and a similarity tree, respectively, according to an embodiment of the present invention. The feature space may be a n-dimensional vector of numerical features that represent gene expression data. For example, the feature space may be based on a chronic obtrusive pulmonary disease ("COPD") study. Genetic data may be obtained from a biological sample (e.g., sputum) from a plurality of patients. The genetic data may be ranked, and a number of highest ranking gene data (e.g., 1000 top ranking gene data) may be used as features for a patient.

FIG. 2E may be a scatter plot of the feature space showing genetic information for an entire patient pool (or a subset of the patient pool). A genetic correlation may be identified between a first phenotype associated with a region 232 (e.g., moderate COPD) and a second phenotype associated with a region 234 (e.g., severe COPD).

FIG. 2F is an illustrative representation of a similarity tree of the feature space showing relationships between genetic information for an entire patient pool (or a subset of the patient pool). Relationships displayed in the similarity tree may indicate that genetic expression plays a role in a particular disease and/or a category of disease (e.g., severe or moderate COPD).

FIGS. 3A-3B are illustrations of associations between an expressed gene of a biological sample and a disease name. In an embodiment, the alternative indication identification application may identify disease names that may be associated with an expressed gene. In another embodiment, the alternative indication identification application may identify expressed genes that may be associated with a disease name.

FIG. 3A shows disease names that may be associated with an expressed gene, according to an embodiment of the present invention. In an embodiment, an expressed gene (e.g., IGF2) may be identified among a set of samples (e.g., from a set of patients) associated with a set of disease names. The alternative indication identification application may determine which disease names are most closely associated with the expressed gene. An association may be established using a chi-squared test and ensuring that an actual value (e.g., actual number of patients with an expressed gene and a disease) is greater than an expected value (e.g., expected number of patients with an expressed gene and a disease). For example, IGF2 may be analyzed for associations with one or more disease names. 7,940 samples may have colorectal neoplasms, 1,805 samples may have both colorectal neoplasms and express the IGF2 gene, and 595.96 samples may be expected to have both colorectal neoplasms and express the IGF2 gene. Thus, IGF2 may be associated with colorectal neoplasms. Although IGF2 may have a known correlation to breast neoplasms, an association with colorectal neoplasms may have been unknown until implementation of the alternative indication identification application. Thus, treatments used for patients with breast cancer (targeting proteins generated by the IGF2 gene) may also be effective for patients with colorectal cancer. For example, an antibody for IGF2 effective for patients with breast neoplasms may also be effective for patients with colorectal neoplasms. By identifying associations between an expressed gene of a biological sample and a disease name, additional uses for medications may be identified.

FIG. 3B shows expressed genes that may be associated with a disease name, according to an embodiment of the present invention. The alternative indication identification application may determine which expressed genes are most closely associated with a disease. For example, expressed genes associated with glioblastoma may be identified. For glioblastoma, IGFBP5 is expressed in 51,177 patients, 879 patients have glioblastoma and express IGFBP5, and 519.01 samples may be expected to have glioblastoma and express IGFBP5. Based on the chi-squared test and ensuring that the actual value exceeds the expected value, an association between glioblastoma and IGFBP5 may be identified. Identifying genes most closely associated with a disease may expose which proteins for which new antibodies should be developed to target the disease.

Figure 4:
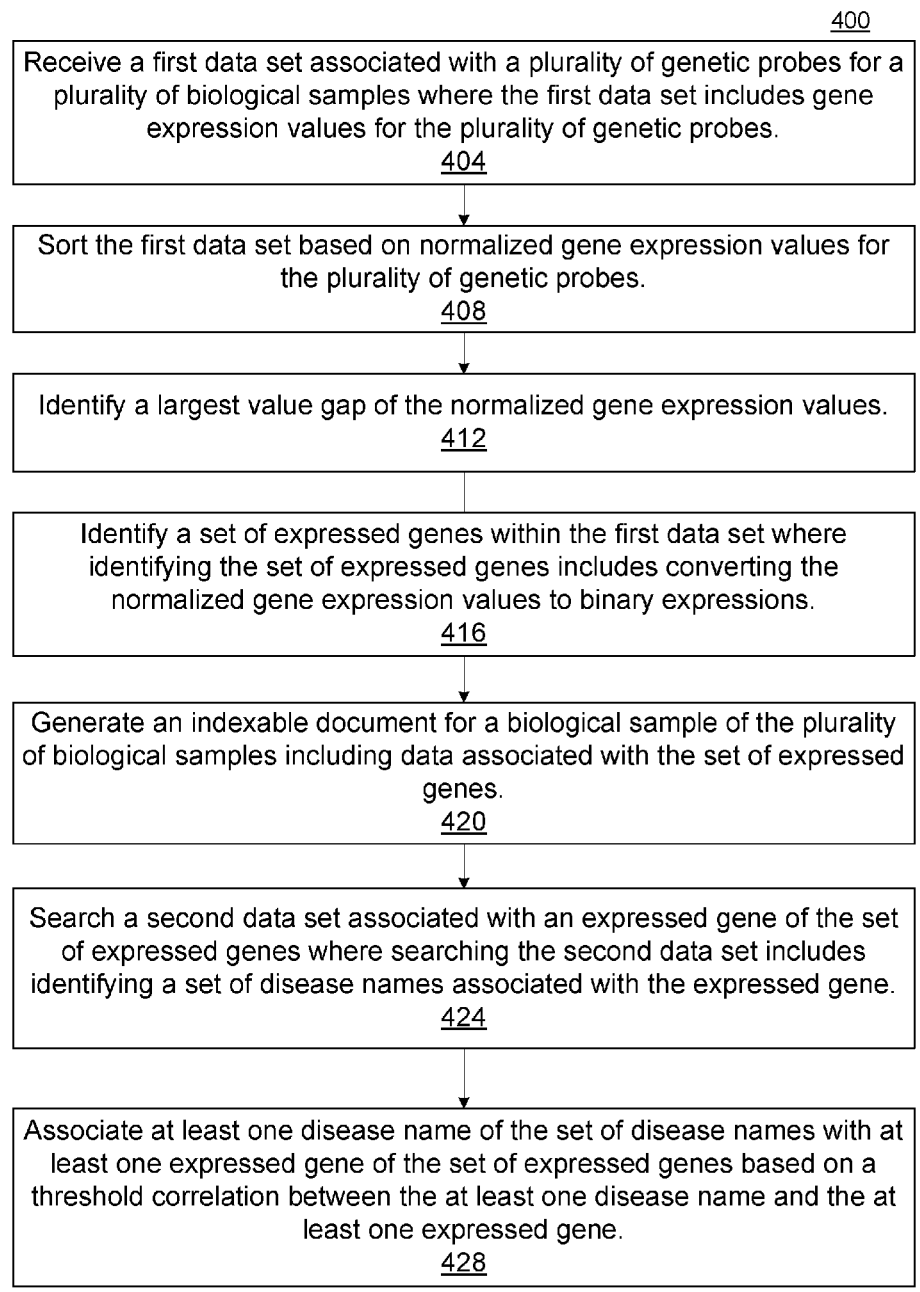
FIG. 4 is a flowchart depicting operational steps of an alternative indication identification application, in accordance with an embodiment of the present invention.

FIG. 4 is a flowchart of a method 400 for associating gene expression data with a disease name, using the alternative indication identification system 100 of FIG. 1, in accordance with an embodiment of the present invention. Steps of method 400 may be executed using a processor of a computer that encompasses, or is part of, alternative indication identification system 100, or another system. In an embodiment, a method of associating gene expression data with a disease name may involve receiving a first data set associated with a plurality of genetic probes for a plurality of biological samples (step 404), sorting the first data set based on a normalized gene expression values for the plurality of genetic probes (step 408), identifying a largest value gap of the normalized gene expression values (step 412), identifying a set of expressed genes within the first data set where identifying the set of expressed genes includes converting the normalized gene expression values to binary expressions (step 416), generating an indexable document for a biological sample of the plurality of biological samples including data associated with the set of expressed genes (step 420), searching a second data set associated with an expressed gene of the set of expressed genes where searching the second data set includes identifying a set of disease names associated with the expressed gene (step 424), and associating at least one disease name of the set of disease names with at least one expressed gene of the set of expressed genes based on a threshold correlation between the at least one disease name and the at least one expressed gene (step 428).

Step 404 may involve receiving a first data set associated with a plurality of genetic probes for a plurality of biological samples. In an embodiment, the first data set may include NCBI GEO data. NCBI GEO data may include rows of gene probes (e.g., GSM550796) and columns of genetic data associated with sequenced biological samples. The gene probes may correspond to one or more genes. The first data may be received via a communication device, such as, for example, a communication device described in FIG. 1. The first data may be stored in a database (e.g., first database 134).

Step 408 may involve sorting the first data set based on a normalized gene expression values for the plurality of genetic probes. In an embodiment, gene expression data in a database (e.g., first database 134) may be sorted. A processor of the computing device 130 (FIG. 1) may sort the probe expression data from highest to lowest for the plurality of biological samples. The plurality of biological samples may be associated with a plurality of patients. The sorted probe expression data may be stored in the first database 134 and/or another database. In an embodiment, a processor of the computing device 130 may omit high and low value outliers from the sorted probe expression data. For example, approximately three high outliers and approximately three low outliers may be omitted.

Step 412 may involve identifying a largest value gap of the normalized gene expression values. In an embodiment, a processor of the computing device 130 may normalize gene expression values by assigning a score for a set of the probe expression data. An assigned score for a set of the probe expression data may be determined by subtracting a lowest non-outlier value from a highest non-outlier value. The score may indicate which genes of the set of probe expression data are most differentially expressed. The top scoring (i.e. the most differentially expressed) set of probe expression data may be used to define a feature space. The feature space may include scored sets of probe expression data in increasing order. The feature space may be stored in the first database 134 and/or another database. By identifying which genes may be most differentially expressed, genes having only small differences across patient populations may be ignored. Genes with only small differences across patient populations may be attributable to noise variables. Thus, by identifying genes that are most differentially expressed, much of the noise may be eliminated and false correlations may be reduced. A gap may be identified between scored sets of gene expression values. For example, a largest value gap may be a greatest difference between consecutive scores. In another example, a largest value gap may be a region most thinly populated (i.e. most sparse region) with scored gene expression values between two regions densely populated with scored gene expression values. In the event of two equally large value gaps or two equally thinly populated regions, a tie breaking protocol may be implemented. The tie breaking protocol may include, for example, selecting the value gap of the equally large value gaps having lower scored sets of gene expression values, selecting the value gap of the equally thinly populated region having lower scored sets of gene expression values, or incorporating and/or omitting one or more outlier gene expression values.

Step 416 may involve identifying a set of expressed genes within the first data set where identifying the set of expressed genes includes converting the normalized gene expression values to binary expressions. The binary expressions may be "expressed" and "unexpressed". Probes having normalized gene expression values above the gap may be identified as expressed. Probes having normalized gene expression values below the gap may be identified as unexpressed.

Step 420 may involve generating an indexable document for a biological sample of the plurality of biological samples including data associated with the set of expressed genes. An indexable document may be generated for a biological sample (e.g., a sample from a patient) of the plurality of biological samples associated with gene expression data. The indexable document may include, for example, text from one or more studies, data associated with a set of expressed genes, and canonical disease names. Indexing the document may include, for example, collecting, parsing, and storing data associated with a biological sample to facilitate information retrieval. The document may be indexed by automatically linking one or more values with one or more other values. The document may be indexed by linking data associated with a biological sample such as, for example, linking gene expression values associated with a biological sample with one or more identified expressed genes associated with a biological sample. In another example, structured data generated from unstructured medical text may be linked with one or more identified expressed genes associated with a biological sample. The indexable document may be indexed by a search server to generate links between values (e.g., identified expressed genes, text of medical studies, canonical disease names, etc.) associated with a biological sample. In an embodiment, the indexable document may include reference data associated with the feature space. The reference data may be used to identify relationships and/or patterns in the gene expression data.

Step 424 may involve searching a second data set associated with an expressed gene of the set of expressed genes where searching the second data set includes identifying a set of disease names associated with the expressed gene. In an embodiment, medical literature (e.g., Medline® text information) may be indexed to enable cross referencing between gene expression data and medical literature. In an embodiment, the indexable document may be combined with indexed medical literature (e.g., Medline® text information). The external medical literature may be unstructured data (e.g., plain language text). The unstructured data may be structured using a natural language processing (NLP) program to make the data accessible to a computing device (e.g., the computing device 130). The NLP program may be a part of the alternative indication identification application or a separate program. In an embodiment, the NLP program may evaluate unstructured data in dependence upon the identified condition evaluations and the logical operators of the unstructured data. That is, the NLP program may determine whether the unstructured data is true in light of the logical operators and evaluations of the condition of a text fragment in the unstructured data. For example, a text fragment may specify conditions including "patient has colorectal neoplasms" and "patient has IGF2 gene" and the logical operator may be an "and" operator. Consider, further, that the indexable document specifies a patient having colorectal neoplasms and the IGF2 gene. In evaluating the conditions, the NLP program may determine that a condition is true, assigning a value of 1 to the condition. In evaluating the text fragment as a whole, the NLP program may determine whether the fragment is true in light of the logical operator. That is, the NLP program determines whether the statement: 1 AND 1 is true. In this example, the NLP program determines that the text fragment is true. In the same way the NLP program assigns a value to the evaluation of the conditions, the NLP module may also assign a value to the evaluation of text fragments. In an embodiment, if a text fragment confirms an identified relationship and/or pattern in the gene expression data, an association may be made, as discussed with respect to step 428 below.

Step 428 may involve associating at least one disease name of the set of disease names with at least one expressed gene of the set of expressed genes based on a threshold correlation between the at least one disease name and the at least one expressed gene. In an embodiment, the alternative indication identification application may identify disease names that may be associated with an expressed gene. In another embodiment, the alternative indication identification application may identify expressed genes that may be associated with a disease name.

Figure 5:
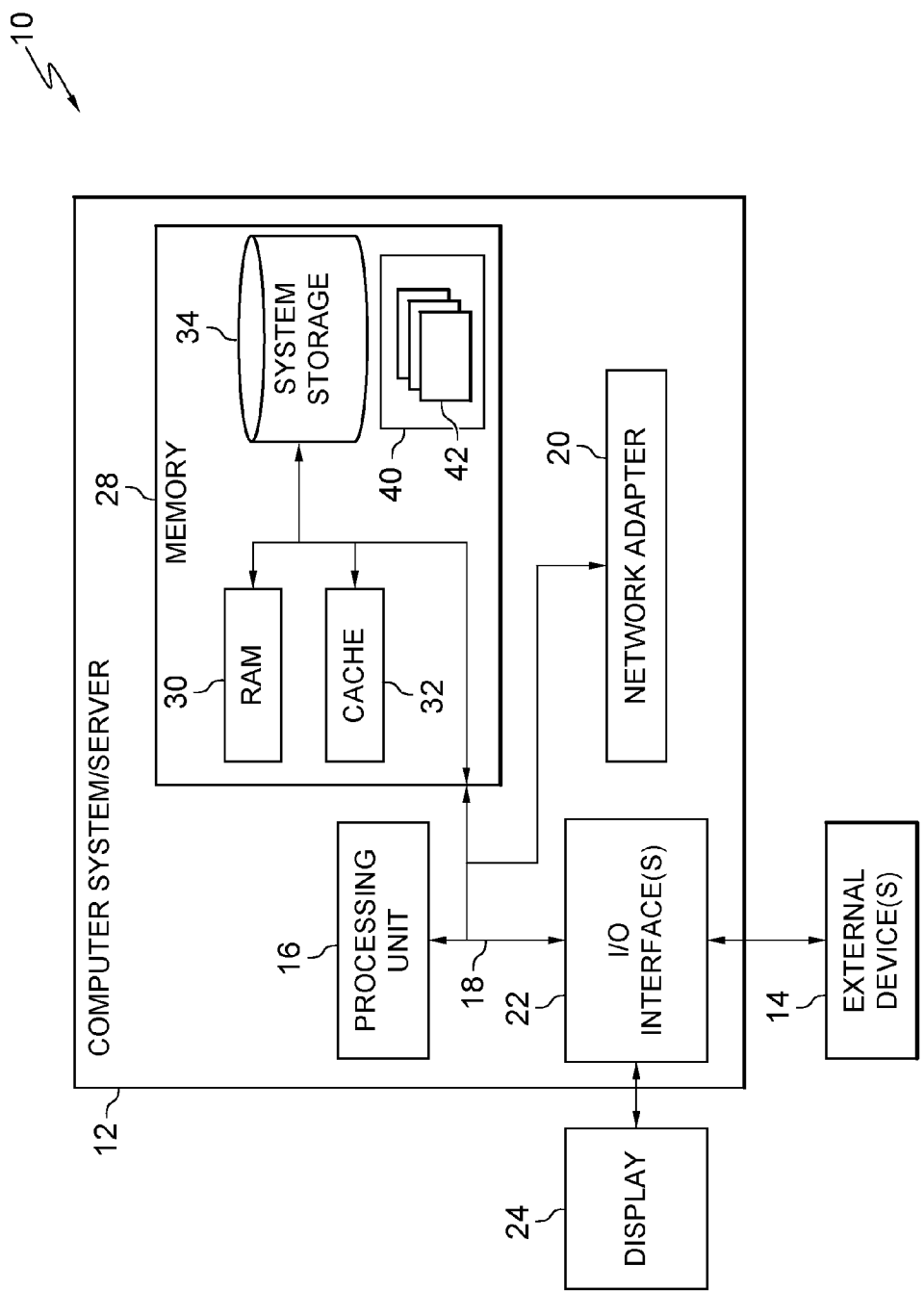
FIG. 5 depicts a block diagram of components of a proxy server computer executing the alternative indication identification application, in accordance with an embodiment of the present invention.
Figure 6:
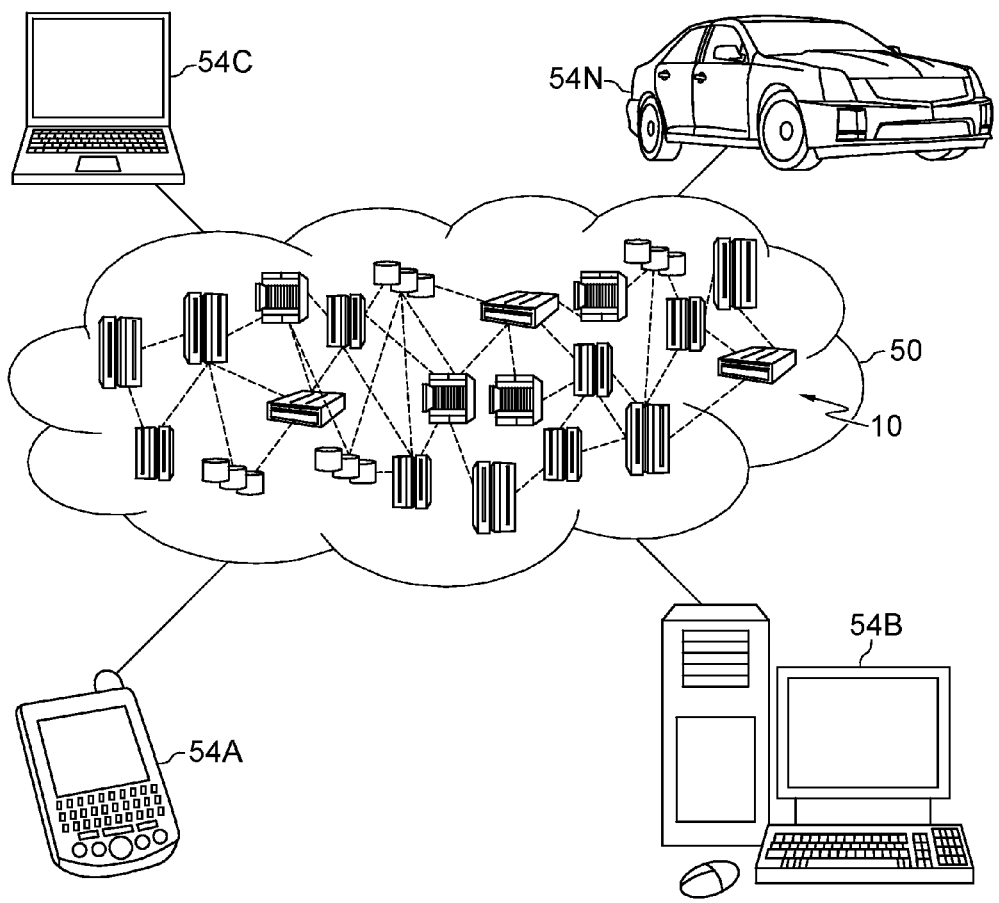
FIG. 6 is a schematic of a cloud computing environment, in accordance with an embodiment of the present invention.

Referring now to FIG. 5, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Referring now to FIG. 5, illustrative cloud computing environment 50 is depicted. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 7:
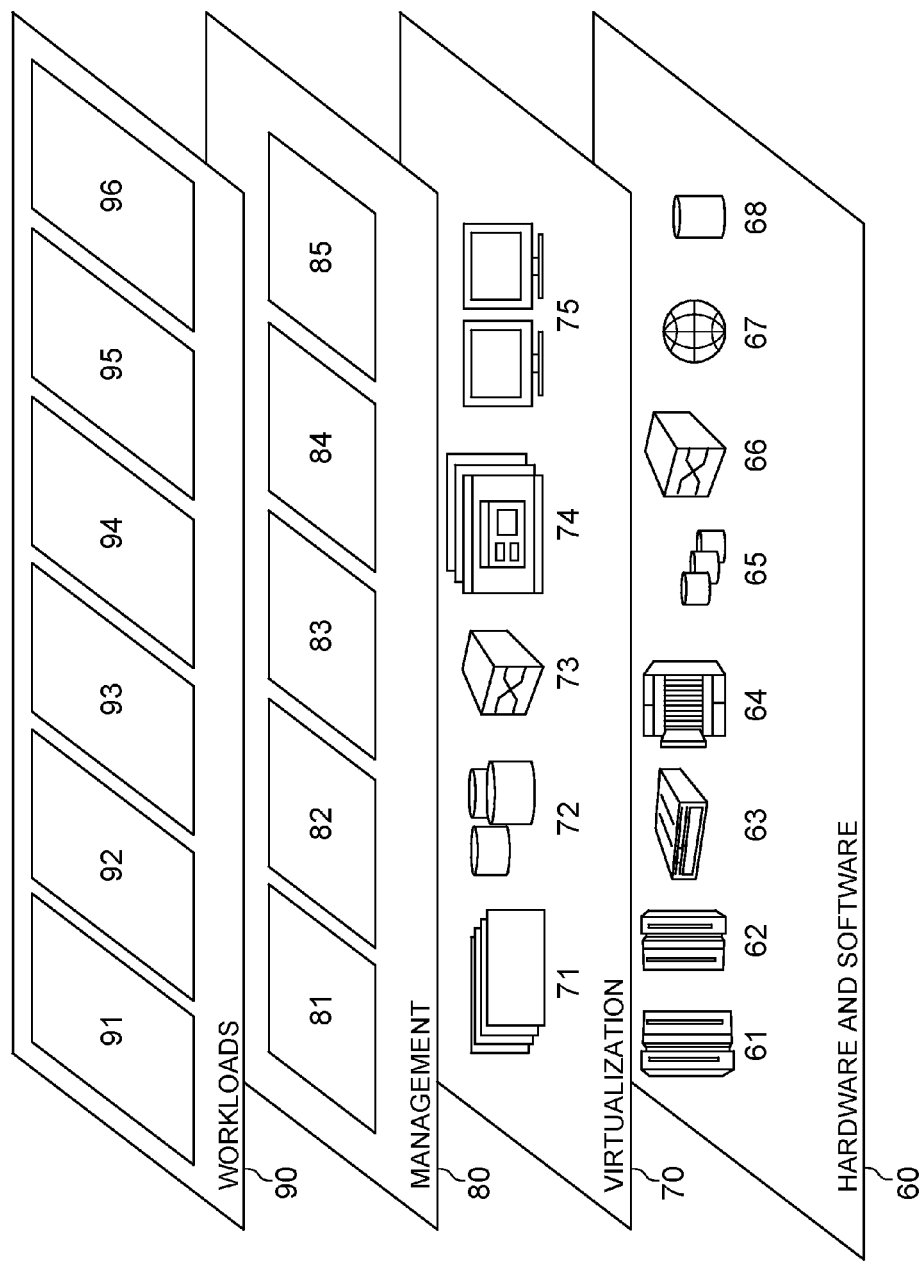
FIG. 7 is a set of abstraction layers provided by the cloud computing environment, in accordance with an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and associating gene expression data with a disease name 96.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

What is claimed is:

1. A method for associating gene expression information with a disease name, the method comprising:
   receiving a first data set associated with a plurality of genetic probes for a plurality of biological samples, wherein the first data set comprises gene expression values for the plurality of genetic probes;
   sorting the first data set based on normalized gene expression values for the plurality of genetic probes;
   identifying a largest value gap of the normalized gene expression values, wherein a gap comprises a difference between two consecutive scores;
   identifying a set of expressed genes within the first data set, wherein identifying the set of expressed genes comprises converting the normalized gene expression values to binary expressions;
   generating an indexable document for a biological sample in the plurality of biological samples comprising data associated with the set of expressed genes;
   searching a second data set associated with an expressed gene of the set of expressed genes, wherein searching the second data set comprises identifying a set of disease names associated with the expressed gene; and
   associating at least one disease name of the set of disease names with at least one expressed gene of the set of expressed genes based on a threshold correlation between the at least one disease name and the at least one expressed gene.

2. The method of claim 1, wherein the first data set is a vector comprising:
   rows representing a number of genetic probes measured by a genetic sequencing apparatus; and
   columns representing genetic information of a number of biological samples.

3. The method of claim 1, wherein the sorting includes assigning a score for the gene expression values by subtracting a lowest non-outlier value from a highest non-outlier value.

4. The method of claim 1, wherein the largest value gap is a largest difference between consecutive scores assigned for the gene expression values.

5. The method of claim 1, wherein a largest value gap is a region having a more sparse population of scored gene expression values than adjacent regions.

6. The method of claim 1, wherein the binary expressions include expressed and unexpressed.

7. The method of claim 1, wherein identifying a set of expressed genes within the first data set comprises:
   identifying gene probes of the plurality of gene probes having a gene expression value greater than the largest value gap as expressed; and
   identifying gene probes of the plurality of gene probes having a gene expression value less than the largest value gap as unexpressed.

8. The method of claim 1, wherein a generated indexable document comprises at least data associated with an expressed gene, and either or both of:
one or more canonical disease names; and
the second data set, wherein the second data set comprises expressed gene data associated with one or more canonical disease names, and wherein the second data set is derived from one or more natural language documents.

9. The method of claim 1, further comprising:
receiving unstructured text associated with one or more medical studies; and generating the second data set by structuring the unstructured text by producing a parse tree based on relationships identified in the content of the unstructured text.

10. A computer program product for associating gene expression information with a disease name, the computer program product comprising a computer readable storage medium having program instructions embodied therewith, wherein the computer readable storage medium is not a transitory signal per se, the program instructions executable by a computer to cause the computer to perform a method comprising:
receiving, by a computer, a first data set associated with a plurality of genetic probes for a plurality of biological samples, wherein the first data set comprises gene expression values for the plurality of genetic probes;
sorting, by a computer, the first data set based on normalized gene expression values for the plurality of genetic probes;
identifying, by a computer, a largest value gap of the normalized gene expression values, wherein a gap comprises a difference between two consecutive scores;
identifying, by a computer, a set of expressed genes within the first data set, wherein identifying the set of expressed genes comprises converting the normalized gene expression values to binary expressions;
generating, by a computer, an indexable document for a biological sample of the plurality of biological samples comprising data associated with the set of expressed genes;
searching, by a computer, a second data set associated with an expressed gene of the set of expressed genes, wherein searching the second data set comprises identifying a set of disease names associated with the expressed gene; and
associating, by a computer, at least one disease name of the set of disease names with at least one expressed gene of the set of expressed genes based on a threshold correlation between the at least one disease name and the at least one expressed gene.

11. The computer program product of claim 10, wherein the first data set is a vector comprising:
rows representing a number of genetic probes measured by a genetic sequencing apparatus; and
columns representing genetic information of a number of biological samples.

12. The computer program product of claim 10, wherein the sorting includes assigning a score for the gene expression values by subtracting a lowest non-outlier value from a highest non-outlier value.

13. The computer program product of claim 10, wherein identifying the set of expressed genes within the first data set comprises:
identifying gene probes of the plurality of gene probes having a gene expression value greater than the largest value gap as expressed; and
identifying gene probes of the plurality of gene probes having a gene expression value less than the largest value gap as unexpressed.

14. The computer program product of claim 10, wherein the generated indexable documents comprise at least one of text from one or more studies, data associated with a set of expressed genes, or canonical disease names.

15. The computer program product of claim 10, further comprising:
receiving unstructured text associated with one or more medical studies; and
generating the second data set by structuring the unstructured text by producing a parse tree based on relationships identified in the content of the unstructured text.

16. A computer system for associating gene expression information with a disease name, the computer system comprising:
one or more computer processors;
one or more computer-readable storage media;
program instructions stored on the computer-readable storage media for execution by at least one of the one or more processors, the program instructions comprising:
instructions to receive a first data set associated with a plurality of genetic probes for a plurality of biological samples, wherein the first data set comprises gene expression values for the plurality of genetic probes;
instructions to sort the first data set based on normalized gene expression values for the plurality of genetic probes;
instructions to identify a largest value gap of the normalized gene expression values, wherein a gap comprises a difference between two consecutive scores;
instructions to identify a set of expressed genes within the first data set, wherein the instructions to identify the set of expressed genes comprises converting the normalized gene expression values to binary expressions;
instructions to generate an indexable document for a biological sample of the plurality of biological samples comprising data associated with the set of expressed genes;
instructions to search a second data set associated with an expressed gene of the set of expressed genes, wherein the instructions to search the second data set comprises instructions to identify a set of disease names associated with the expressed gene; and
instructions to associate at least one disease name of the set of disease names with at least one expressed gene of the set of expressed genes based on a threshold correlation between the at least one disease name and the at least one expressed gene.

17. The system of claim 15, wherein the first data set is a vector comprising:
rows representing a number of genetic probes measured by a genetic sequencing apparatus; and
columns representing genetic information of a number of biological samples.

18. The system of claim 15, wherein the instructions to sort include instructions to assign a score for the gene expression values by subtracting a lowest non-outlier value from a highest non-outlier value.

19. The system of claim 15, wherein the instructions to identify the set of expressed genes within the first data set comprise:
- instructions to identify gene probes of the plurality of gene probes having a gene expression value greater than the largest value gap as expressed; and
- instructions to identify gene probes of the plurality of gene probes having a gene expression value less than the largest value gap as unexpressed.

20. The system of claim 15, further comprising:
- receiving unstructured text associated with one or more medical studies; and
- generating the second data set by structuring the unstructured text by producing a parse tree based on relationships identified in the content of the unstructured text.

* * * * *